United States Patent [19]

Shields

[11] Patent Number: 5,350,368
[45] Date of Patent: Sep. 27, 1994

[54] TETHERED BUTTERFLY NEEDLE TRAP

[76] Inventor: Jack W. Shields, 1950 Las Tunas Rd., Santa Barbara, Calif. 93103

[21] Appl. No.: 993,236

[22] Filed: Dec. 17, 1992

[51] Int. Cl.$^5$ .............................................. A61M 5/00
[52] U.S. Cl. ................................. 604/263; 604/177; 604/198
[58] Field of Search ............... 604/192, 198, 263, 177; 128/919

[56] References Cited

U.S. PATENT DOCUMENTS

| | | | |
|---|---|---|---|
| 4,927,415 | 5/1990 | Brodsky | 604/164 |
| 4,935,011 | 6/1990 | Hogan | 604/177 |
| 4,941,881 | 7/1990 | Masters et al. | 604/162 |
| 5,030,212 | 7/1991 | Rose | 604/263 |
| 5,061,250 | 10/1991 | Shields | 604/198 |
| 5,069,341 | 12/1991 | Barbieri et al. | 206/365 |
| 5,112,311 | 5/1992 | Utterberg et al. | 604/177 |
| 5,120,320 | 6/1992 | Fayngold | 604/177 |
| 5,137,515 | 8/1992 | Hogan | 604/110 |
| 5,192,275 | 3/1993 | Burns | 604/263 |
| 5,197,956 | 3/1993 | Brizulla | 604/171 |
| 5,219,339 | 6/1993 | Saito | 604/198 |

FOREIGN PATENT DOCUMENTS 425448  5/1991  European Pat. Off. ............ 604/110

Primary Examiner—C. Fred Rosenbaum
Assistant Examiner—V. Alexander

[57] ABSTRACT

A a device for preventing inadvertent needle stick injuries from hollow-bore steel needles on the leading ends of winged or "butterfly" infusion assemblies. The device comprises a puncture-resistant semi-flexible conical tube which slides over tubing trailing from the butterfly needle hub to safely entrap the needle by means of the wings when the user holds a leading tether firmly over a vein with one hand, and pulls back on the tailing tubing with the other, such that the wings slide backward through paired slits until trapped within slots in said cone whose leading end forms a tether on the superior surface and a horizontal V-shaped aperture on the inferior surface leading to the paired slits and slots. The trailing end of said cone is adjusted to releasably grasp the trailing tubing, or the trailing paraphernalia to which the tubing is attached, such that the device remains out of the way during insertion and intended usage of the leading hollow-bore steel needle.

5 Claims, 2 Drawing Sheets

U.S. Patent      Sep. 27, 1994      Sheet 1 of 2      5,350,368
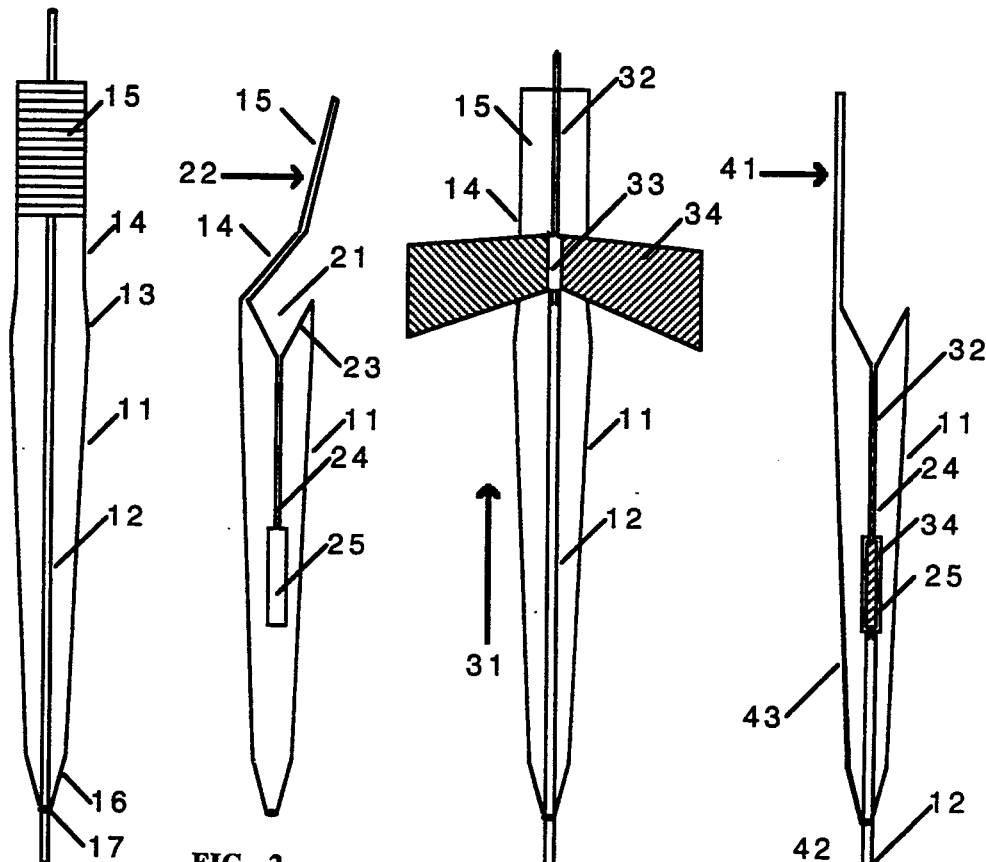
FIG. 2
FIG. 3
FIG. 4
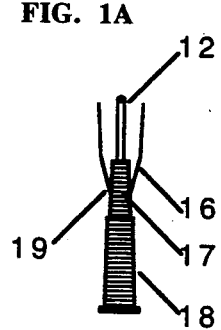
FIG. 1A
FIG. 1B

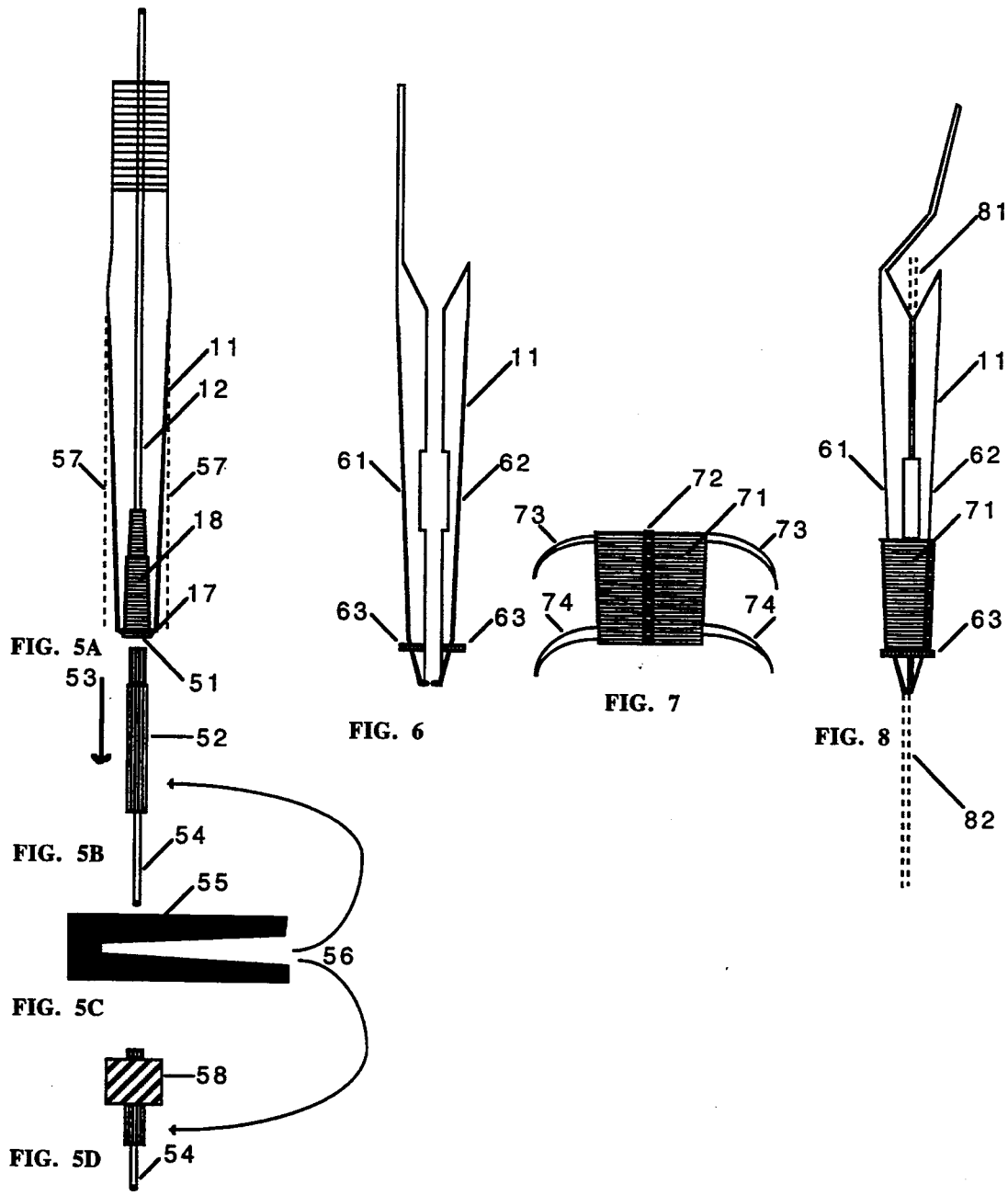

TETHERED BUTTERFLY NEEDLE TRAP

BACKGROUND OF THE INVENTION

1. Field of the Invention

This invention relates to the prevention of accidental hollow-bore needle-stick injuries in health care workers using winged infusion assemblies for administering fluid medications in veins or withdrawing blood.

2. Description of Prior Art

To prevent needle-stick injuries to health care workers, needle guards which slide over syringes to extend beyond the tip of an injection needle and,then, lock are now common. Guards which slide over the trailing tubing in infusion assemblies are less well developed than those which slide and lock over syringes. However, the former are crucial in preventing transmissible blood-borne infections, because the leading needles are usually inserted into veins and, therefore, usually bring back blood in their bores on withdrawal.

The use of tethers as parts of needle guards have been described by Slaughter (U.S. Pat. No. 4,781,697 Nov. 1, 1988), Dombrowski et al (U.S. Pat. No. 4,790,828 Dec. 13, 1988), Corey (U.S. Pat. No. 4,955,866 Sep. 11, 1990), and Simon (U.S. Pat. No. 5,051,109 Sep. 24, 1991). None of these describe a tether which uses the patient as an anchor.

In U.S. Pat. No. 5,061,250 Oct. 29, 1991, Shields described a tether with a tab finger-held over a vein aligned pull a slit elastomeric tube containing a puncture-resistant sheath over a needle during withdrawal. This system was complex and awkward to owing to orientation of the slit which captures the needle, the elastomeric nature of the system, and lack of provision for keeping the tether out of the way when not in use. The previous invention is not applicable to the instant invention, because the latter does not incorporate a slit elastomeric tube.

In U.S. patent application 07/956/790 filed Oct. 5, 1992, Shields described a tethered cylindrical or conical tube with a leading end designed to safely entrap the hub and leading end of a hollow-bore steel needle whose trailing end is attached to proximal tubing. The instant invention differs from the former in that a conical tube with a leading tether embodies a V-shaped opening beneath the tether; paired longitudinal slits terminating in slots designed to trap the wings of a butterfly infusion assembly within the body of said cone, such that the leading hollow-bore steel needle can be safely trapped; and a variably sized trailing aperture in the trailing end of said cone, such that the device can be releasably stabilized, either with respect to the tubing over which said cone slides or to the paraphernalia on the trailing end of said tubing.

Owing to the alarming rate of increase in HIV, HBV and HCV infections in health care workers caused by accidental hollow-bore needle sticks after withdrawal of the needles from the veins of infected patients, urgent needs now exist for safer equipment, especially paraphernalia used for giving intravenous infusions or withdrawing blood.

SUMMARY

The object of this invention is to provide and teach novel methods whereby health care workers can withdraw sharp hollow-bore steel needles from the veins of patients without exposing the points.

Another object is to provide systems for withdrawing blood or giving infusions which can be handled like counterparts commonly used, without encumbrance from apparata intended to prevent accidental needle sticks.

A third object is to provide systems which are simple, reliable, efficient and easy to use with both hands kept in customary, as well as safe positions during and after needle withdrawal.

A fourth object is to protect by-standers and health care personnel responsible for the disposal of tubing with needles still attached.

A final object is to provide a needle safety system which can be manufactured easily and put to critical care use almost immediately, especially on phlebotomy and intravenous infusion equipment whose leading ends are fitted with winged or "butterfly" hubs. (See Drawings).

BRIEF DESCRIPTION OF THE DRAWINGS

FIG. 1A is a diagrammatic axial section of a conical butterfly needle trap showing the infusion tubing passing through. (Scale 1″: 1″ in all drawings).

FIG. 1B is an axial section showing the trailing end of the conical trap releasably attached to the leading end of the hub on the wailing end of the tubing.

FIG. 2 is a diagrammatic axial section of the conical butterfly needle trap shown in FIG. 1A, but without enclosed infusion tubing and rotated 90° to the left.

FIG. 3 is a an axial section of the conical butterfly needle trap like that in FIG. 1A showing the butterfly needle wings partially pulled into paired slits by traction on the trailing tubing.

FIG. 4 is an axial section like that in FIG. 2, showing the butterfly needle wings trapped within paired slots in the body of the conical trap.

FIG. 5A is an axial section like that in FIG. 1, showing a trailing aperture in the cone large enough to allow passage of a standard needle hub therethrough.

FIG. 5B is an axial section like that in FIG. 1, showing an aligned luer-slip hub.

FIG. 5C is a diagrammatic illustration of a supplementary useful clamp.

FIG. 5D is an axial section like that in FIG. 1, showing an aligned Luer-Lok hub.

FIG. 6 is an axial section like that in FIG. 2, showing the cone bisected.

FIG. 7 depicts a hinging clamp for reconstituting the bisected cone.

FIG. 8 shows the reconstituted cone enclosing infusion tubing.

DESCRIPTION OF PREFERRED EMBODIMENTS

A first preferred embodiment of this tethered butterfly needle trap is shown in FIGS. 1-4. As shown in FIG. 1A, the trap consists of a conical semi-rigid puncture-resistant tube, hereinafter called a cone (11), which slides over flexible intravenous infusion tubing, hereinafter referred to as tubing (12). The leading end of the cone is cut away underneath and diagonally at point (13) to leave a flexible tether (14) whose superior leading surface (15) is made rough to increase friction when grasped or held down by a finger. The trailing end of the cone (16) narrows sharply to leave a trailing aperture (17) whose diameter is slightly smaller than the external diameter of the tubing (12).

As shown in FIG. 1B, the trailing end of the tubing (12) is permanently attached to the leading end of a hub (18). In winged infusion assemblies wherein the tubing is of small diameter, the trailing aperture (17) in the trailing end of the cone (16) is optionally made larger, such that it releasably grasps the leading conical part of the needle hub (19), instead of the tubing.

As shown at a 90° angle in FIG. 2, the leading cutaway portion of the cone (11) leaves a flexible tether (14) whose leading end (15) swings over the leading mouth (21) of the cone when downward pressure is applied in the direction of the arrow at (22). An additional diagonal cut (23) into the leading end of the cone leaves a horizontal V-shaped aperture leading to symmetrically paired longitudinal slits (24) which terminate in symmetrically paired slots (25) capable of symmetrically conveying and, then, trapping the paired wings of a butterfly needle.

As shown in FIG. 3, when the cone (11) is slid forward over the tubing (12) in the direction of the arrow at (31), the leading tether (14-15) will come to rest over the skin-submerged hollow-bore steel needle (32); while the exposed hub (33) and wings (34) of the butterfly needle will come to rest in the open V-shaped mouth (21) of the cone shown in FIG. 2.

As shown at a 90° angle in FIG. 4, when a finger of one hand presses downward in the direction of the arrow at (41) to prevent venous bleeding, as well as stabilize the tether; while the other hand pulls back the trailing tubing in the direction of the arrow at (42), the resultant forces will retract the paired butterfly wings (34) through the paired slits (24) until the wings become trapped in the paired slots (25). Then, the hollow-bore steel needle (32-dotted lines) will be effectively enclosed within the confines of the cone (11), such that its sharp tip or shaft will not be exposed after use tier the intended purposes of conveying infusions or withdrawing blood.

It should be added that making the cone thinner at its leading end and thicker at its trailing end, as depicted by line thickness at (43) in FIG. 4 and included in FIGS. 5-6 will lend more flexibility at the leading end for the tether (14), lower part of the V-shaped opening (23) and the slit (24); while lending more stability to the slot (25) and closure of the slit (24) after the wings (34) have passed through into the slot (25).

To operate this tethered butterfly needle trap, the user manipulates the leading winged infusion needle just like he/she would do under customary circumstances by hooking up the trailing hub (18) to connectors emanating from an infusion bag or bottle; flushing air from the assembly; removing the customarily supplied scabbard from the hollow-bore steel infusion needle; inserting the needle into a well-chosen vein; and giving the infusion or series of infusions. However, when it's time to withdraw the needle from the vein of a patient, the user will grasp the leading tether (14,15); pull the cone (11) forward until the lower V-shaped portion (23) slides under the hub (33) of the butterfly; place a sterile pledget over the venepuncture site; press down on the roughened leading end of the tether (15); and, then, pull back on the trailing tubing (12) until the hollow-bore steel needle is trapped within the slot (25) in the cone (11) by means of its paired wings (34). In addition, to "fail-safe", it is wise to slide the originally supplied scabbard back over the hollow-bore steel needle (32) in the event that the needle is inclined to wobble enough to exit the slit, or the event that co-workers are careless during disposal of this tethered butterfly needle trap.

In a second preferred embodiment, as shown in FIG. 5A, the trailing aperture (17) in the cone (11) is made larger in internal diameter than the external diameter of the trailing flanged end (51) of the hub (18) permanently attached to the trailing end of the tubing (12), e.g. >7.5 mm.; as well as greater than that of the largest external diameter of the fitting luer-slip connector (52), shown below in FIG. 5B. As results, the cone (11) will slide proximally over the luer-slip connector (52) in the direction of the arrow (53) until an object of even larger external dimension is encountered along the proximal course of the tubing (54). Supplemental provision of an open-ended clamp (55), shown in FIG. 5C, designed to clasp over the luer-slip connector (52) in the direction of the arrow (56) will prevent forward sliding of the retracted cone and keep said cone even more remote from the winged infusion needle before and during the intended use without interfering with flow through the essential tubing. After the winged infusion needle is used for its intended purposes, the clamp (55) can be removed to allow free sliding of the cone (11) forward over distal tubing (12) until the cone and its leading parts shown in FIGS. 1-4 become useful for enclosing the hollow-bore steel needle (32).

In a third preferred embodiment, as shown by the dotted lines (57) in FIG. 5A, the cone can be made cylindrical, such that it will allow passage therethrough of an aligned Luer-Lok hub (58), as shown in FIG. 5D. Again, an open ended clamp (55) applied in the direction of the arrow (56) will prevent the cylinder (57) from sliding over the Luer-Lok hub (58) until the leading parts of the cone (11) are needed for enclosing the hollow-bore steel needle.

In a fourth preferred embodiment (not illustrated), the cone can be made ovoid, instead of round, especially at the leading end. This modification in the shape of the opening shown at (21) beneath the tether (14,15) in FIG. 2 will decrease the angle at which the paired wings (34) on the butterfly needle hub (33) enter the paired slits (24) in the cone (11) when the trailing tubing (12) is manually retracted.

In a fifth, but not necessarily preferred embodiment, the cone can be laser-slit to the trailing end or molded in two matching parts securely apposed by means of a clasping mechanism, as shown diagrammatically in FIGS. 6-8. This modification will allow application of the conical needle trap to "butterfly" infusion needles already assembled by various manufacturers. For instances: as shown in FIG. 6, the cone (11) can be slit into or molded in two parts (61 and 62), each supplied with a flange (63) on the outside of the trailing end. As shown in FIG. 7, a rigid clasp (71) with a central hinge (72) and mutually embracing arms (73,74) can hold the two half-cones together. As shown in FIG. 8, when the rigid conical clasp (71) is secured to reconstitute the full cone (11), forward movement will be stopped by the diameter of the cone; while backward slipping will be stopped by the flange (63). Thus constituted to surround the trailing infusion tubing on a winged needle hub depicted by leading (81) and trailing (82) dotted lines, the reconstituted cone will serve as shown previously in FIGS. 1-4, and as outlined verbally in the first preferred embodiment.

While it would seem that polypropylene or tygon would be optimal materials from which to mold such cones currently, it will be appreciated by those skilled in the art that variations in materials, dimensions and details can be made without departing from the spirit of this invention. Finally, it should be mentioned that these specifications supplement those set forth in U.S. patent application No. 07/956,790 filed Oct. 5, 1992 with respect to tether attachment, texture, opening forms, body configuration and trailing end modifications.

Therefore, I claim:

1. A tethered trap for safely shielding a hollow-bore steel needle having a winged hub assembly and trailing cylindrical tubing attached thereto; said tethered trap comprising a puncture-resistant, semi-rigid hollow cone; said tethered trap being internally dimensioned to slide over said trailing cylindrical tubing, and wherein said tethered trap further comprises:

(a) an open leading end resembling an open mouth with an internal diameter larger than the external diameter of the hub of said winged hub assembly, V-shaped recesses on each side, and a superior leading surface extending to form a flexible tether;

(b) an open trailing end with an internal diameter less than the internal diameter of said open leading end, and nearly equal to or greater than the external diameter of said trailing cylindrical tubing, (c) a body portion between said leading and said trailing end, said body portion having symmetrically paired horizontal slits extending from said V-shaped recesses to terminate in paired horizontal slots, the combined length of said slits and slots being greater than the distance between the leading tip of said hollow-bore steel needle and the trailing edges of the wings in said winged hub assembly, the width of said slots being greater than the thickness of each wing in said winged hub assembly, and the length of said slots being greater than the distance between the leading and said trailing edges of said wings where enclosed in said paired horizontal slots.

2. Said tethered trap, as in claim 1, further comprising said puncture-resistant, semi-rigid hollow cone with a material thickness substantially greater in the trailing end of said body portion.

3. Said tethered trap, as in claim 1, further comprising said trailing open end with an internal diameter greater than the external diameter of paired flanges on a standard hub permanently attached to the trailing end of said trailing cylindrical tubing attached to said winged hub assembly.

4. Said tethered trap, as in claim 1 further comprising said trailing open end with internal diameter or configuration suited to temporarily grasp the leading conical end of said standard hub attached to said trailing end of said trailing cylindrical tubing.

5. Said tethered trap, as in claim 1, further comprising said trailing open end with configuration compatible with temporary immobilization of said tethered trap by paraphernalia appended to said trailing cylindrical tubing or to cylindrical tubing trailing said standard hub attached to said trailing cylindrical tubing attached to said winged hub assembly.

* * * * *